(12) United States Patent
Krafft et al.

(10) Patent No.: US 6,713,029 B1
(45) Date of Patent: Mar. 30, 2004

(54) STERILIZATION TRAY

(75) Inventors: Petrus Krafft, Warsaw, IN (US); Shane E. Maust, Milford, IN (US)

(73) Assignee: Zimmer Technology, Inc., Chicago, IL (US)

( * ) Notice: Subject to any disclaimer, the term of this patent is extended or adjusted under 35 U.S.C. 154(b) by 517 days.

(21) Appl. No.: 09/658,701

(22) Filed: Sep. 8, 2000

(51) Int. Cl.$^7$ .................................................. A61L 2/00
(52) U.S. Cl. ...................... 422/300; 206/370; 206/438; 220/529; 220/735; 422/297
(58) Field of Search .............................. 422/297, 300; 206/370, 438; 220/529, 735

(56) References Cited

U.S. PATENT DOCUMENTS

| | | | |
|---|---|---|---|
| 5,340,551 A | * | 8/1994 | Berry, Jr. .................... 422/300 |
| 5,492,671 A | * | 2/1996 | Krafft .......................... 422/26 |
| 5,540,901 A | | 7/1996 | Riley et al. |
| 5,882,612 A | | 3/1999 | Riley et al. |
| 6,099,812 A | * | 8/2000 | Allen et al. ................. 422/300 |

* cited by examiner

*Primary Examiner*—Krisanne Thornton
(74) *Attorney, Agent, or Firm*—Jonathan D. Feuchtwang; Zimmer Technology, Inc.

(57) ABSTRACT

A sterilization tray has a smooth exterior, ruggedness, light weight, high thermal conductivity, comfortable gripping surfaces, stackability, and low cost construction. The tray is constructed of stamped and folded sheet metal, but in such a way as to provide rounded corners. A molded handle insert is attached to the ends of the tray to provide the multiple utility of reducing the number of handles required, maximizing space utilization, providing a comfortable gripping surface on the outside and inside of the tray, and providing stackability.

17 Claims, 4 Drawing Sheets

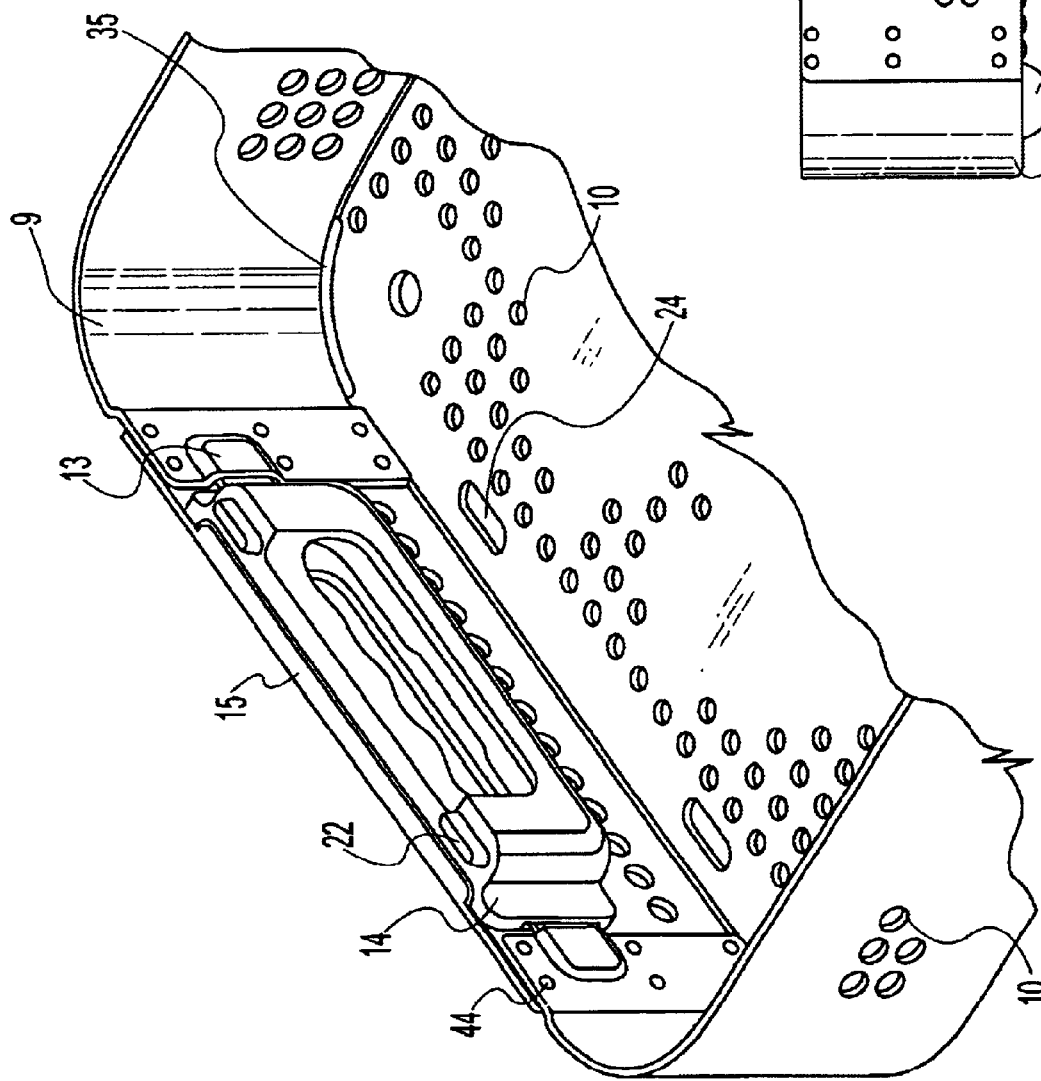
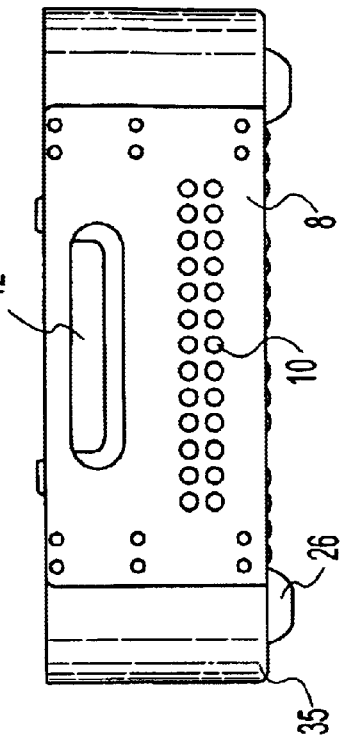

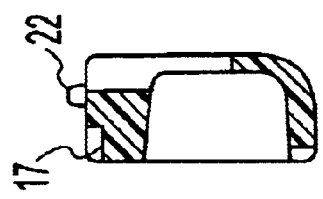
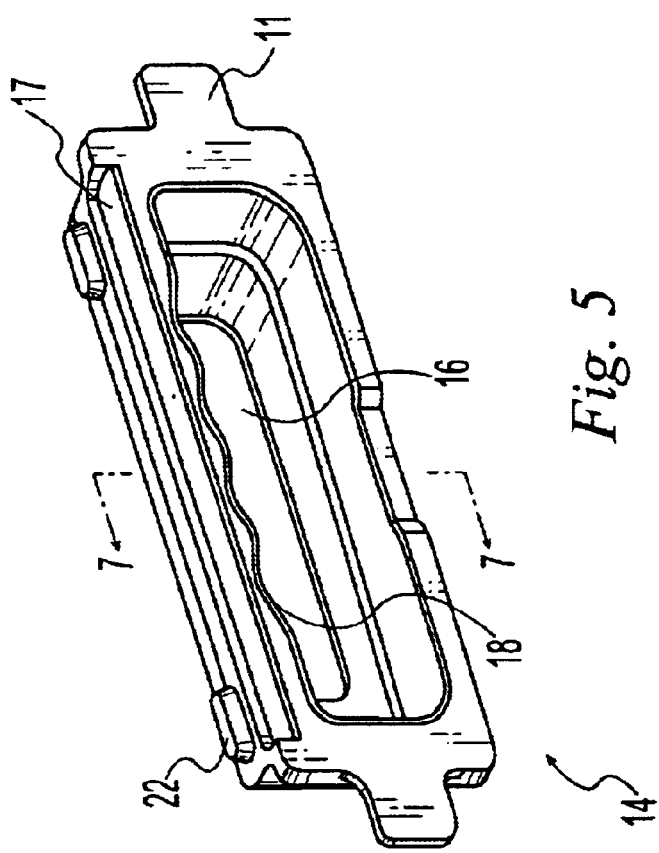
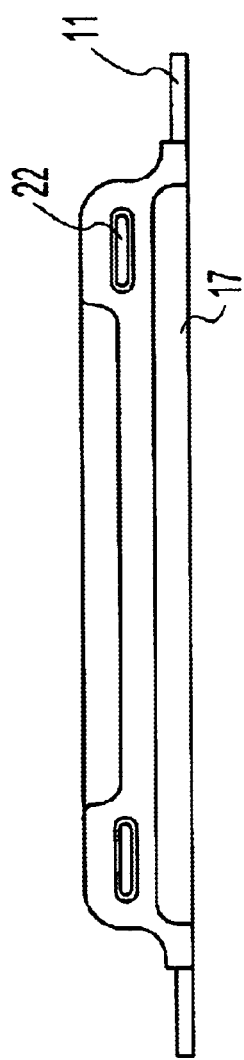

STERILIZATION TRAY

BACKGROUND OF THE INVENTION

The invention relates to a sterilization tray.

Surgical instruments are typically stored, transported and prepared for use in sterilization trays. The trays include rigid enclosing walls to provide protection. The walls are typically perforated with multiple holes to allow ingress and egress of a sterilant, e.g. steam, when the tray is placed in a sterilizer. Typically, the trays are wrapped in paper or cloth to maintain the sterility of the contents in storage. It is desirable for the trays to have smooth exteriors, e.g. rounded corners, ruggedness, light weight, high thermal conductivity, and low cost construction. U.S. Pat. No. 5,882,612 teaches a sterilization tray having plastic end panels or corner pieces to simplify the construction of the tray. The patent points out that trays are typically constructed of stamped and folded sheet metal and that it is extremely difficult, if not impossible, to produce a tray with rounded corners using such a construction.

It is further desirable for the trays to have comfortable gripping surfaces and stackability. Increasingly, such trays are used in conjunction with European DIN standard storage containers. A typical DIN container will contain one or more trays stacked within it. Typical prior art trays include one set of handles for lifting the tray from the DIN container and a second set of handles for carrying the tray.

SUMMARY OF THE INVENTION

The present invention provides a sterilization tray having a smooth exterior, ruggedness, light weight, high thermal conductivity, comfortable gripping surfaces, stackability, and low cost construction. The tray is constructed of stamped and folded sheet metal, but in such a way as to provide rounded corners. This construction makes a rugged, lightweight, and low cost tray. A molded handle insert is attached to the ends of the tray to provide multiple utility of reducing the number of handles required, maximizing space utilization, providing a comfortable gripping surface on the outside and inside of the tray, and providing stackability.

BRIEF DESCRIPTION OF THE DRAWINGS

FIG. 2 is a perspective view of the inside of the tray of FIG. 1.

FIG. 3 is a side plan view of the tray of FIG. 1.

FIG. 5 is a perspective view of a handle insert component used in the tray of FIG. 1.

FIG. 6 is a top plan view of the handle insert component of FIG. 5.

FIG. 7 is a side sectional view of the handle insert component taken along line 7—7 of FIG. 5.

DETAILED DESCRIPTION OF THE INVENTION

Figure 1:
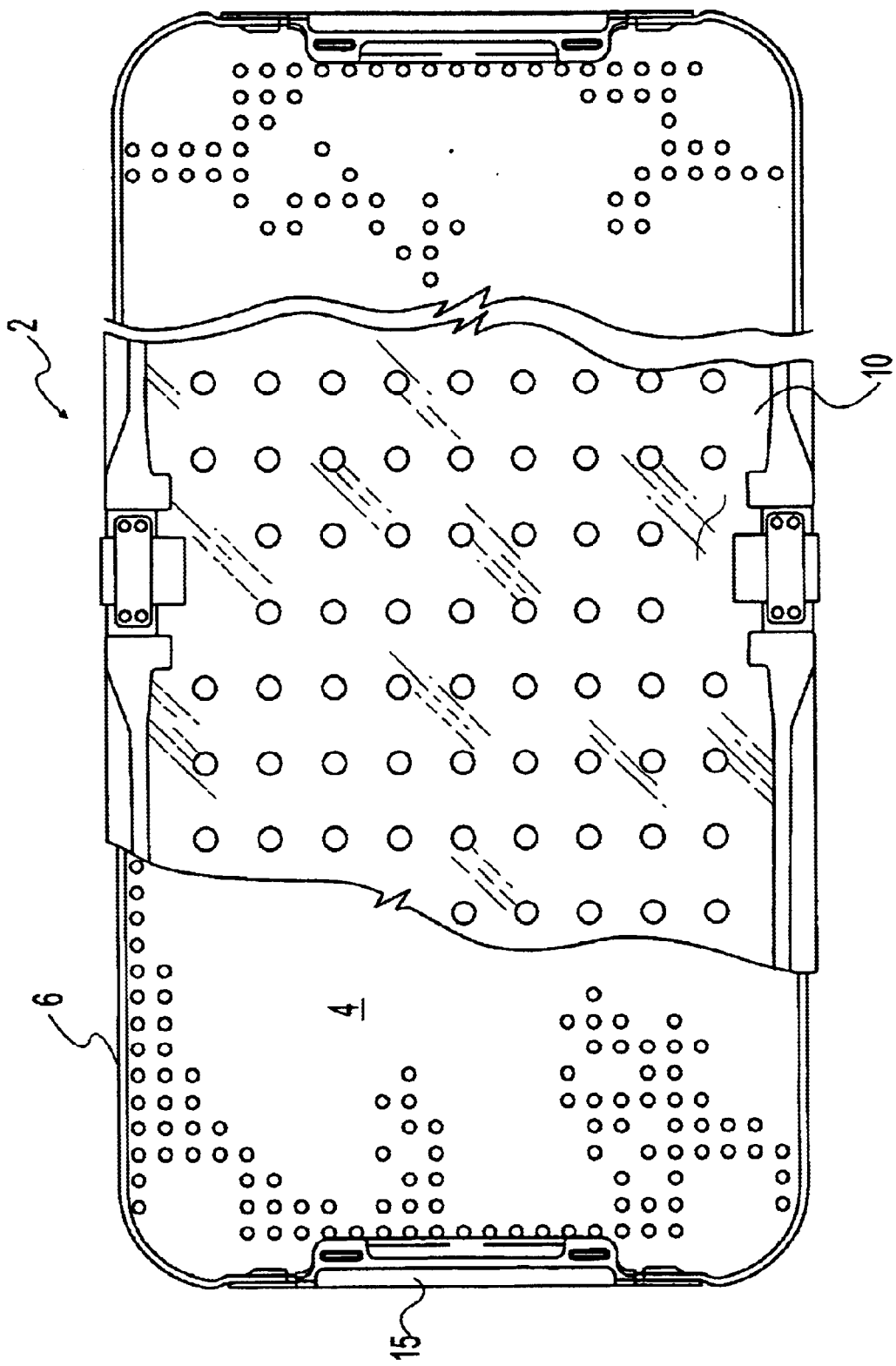
FIG. 1 is a top plan view of a sterilization tray according to the present invention.

FIGS. 1–3 depict an exemplary embodiment of a sterilization tray 2 according to the present invention. The tray 2 includes a bottom wall 4, upstanding side walls 6, and upstanding end walls 8. The walls are joined together to form an open box having rounded corners 9. The walls include perforations 10 for allowing sterilant, e.g. steam, in and out of the tray. The interior of the tray may include various racks and fixtures for holding instruments as is known in the art. A lid 10 is removably secured to the tray to cover the open top. Preferably the tray is made of a lightweight, thermally conductive, and strong material such as sheet metal, e.g. aluminum. The lid 10 can also be made of sheet metal. However, it is preferably made of a transparent material such as plastic. Each end wall 8 includes elongate handle aperture 12 forming a handle in the sheet metal. A handle insert 14 is attached adjacent the aperture 12. Preferably the handle insert is attached on the inside of the tray so as to maintain a smooth exterior surface on the tray. Attachment ears 11 formed on the handle insert 14 extend into slots 13 formed in the end wall 8 to secure the handle insert 14 to the end wall 8. An upper portion 15 of the end wall extends over a portion of the handle insert 14 to reinforce the attachment of the handle insert 14 to the end wall 8. The upper portion 15 of the end wall adds lifting strength to the handle insert 14.

The handle insert 14 includes a grip aperture 16 bounded on the top by a gripping surface 18. The gripping surface has a thickness greater than the thickness of the end wall 8 such that the gripping surface distributes the weight of the tray over a greater area of the users fingers and thus providing a more comfortable handle than the aperture 12 alone. Scalloped fingergrips 20 are advantageously formed in the grip surface 18. Preferably the aperture 16 extends through the handle insert so that it can be gripped from the inside or outside of the tray. Preferably the handle insert is a low cost, light weight, molded plastic part. An example of a suitable plastic for use in this application is Radel® R polyphenylsulfone manufactured by BP Amoco Chemicals. This material has high strength and can be repeatedly autoclaved.

The extra grip thickness and double sidedness of the handle insert 14 is further advantageous where the tray is to be inserted into another container, e.g. a DIN container. When the tray is inserted into such a container with the end wall 8 closely adjacent the end wall of the container, there is insufficient room to position fingers on the outside of the tray 2 and extend the fingers through the aperture 12 to lift the tray. Likewise, because of the close proximity of the container wall to end wall 8, without handle insert 14 there would be insufficient space to extend the fingers through the aperture 12 and lift the tray. However, handle insert 14 provides a grip surface 18 that permits a secure grip on the tray from the inside without the fingers needing to extend past aperture 12.

The handle insert 14 also includes stacking lugs 22 extending upwardly above the top edge of the walls. Corresponding stacking lug receiving holes 24 are formed in the bottom wall 4 of the tray. Thus, when one tray is stacked on another, stacking lug 22 is received in hole 24 to keep the trays from sliding relative to one another.

Tray feet 26 are provided on the outside corners of the bottom wall 4 to space the bottom wall 4 away from a support surface to facilitate circulation of sterilant through the perforations 10. Preferably the feet are made of a molded plastic material such as Radel® R.

Figure 4:
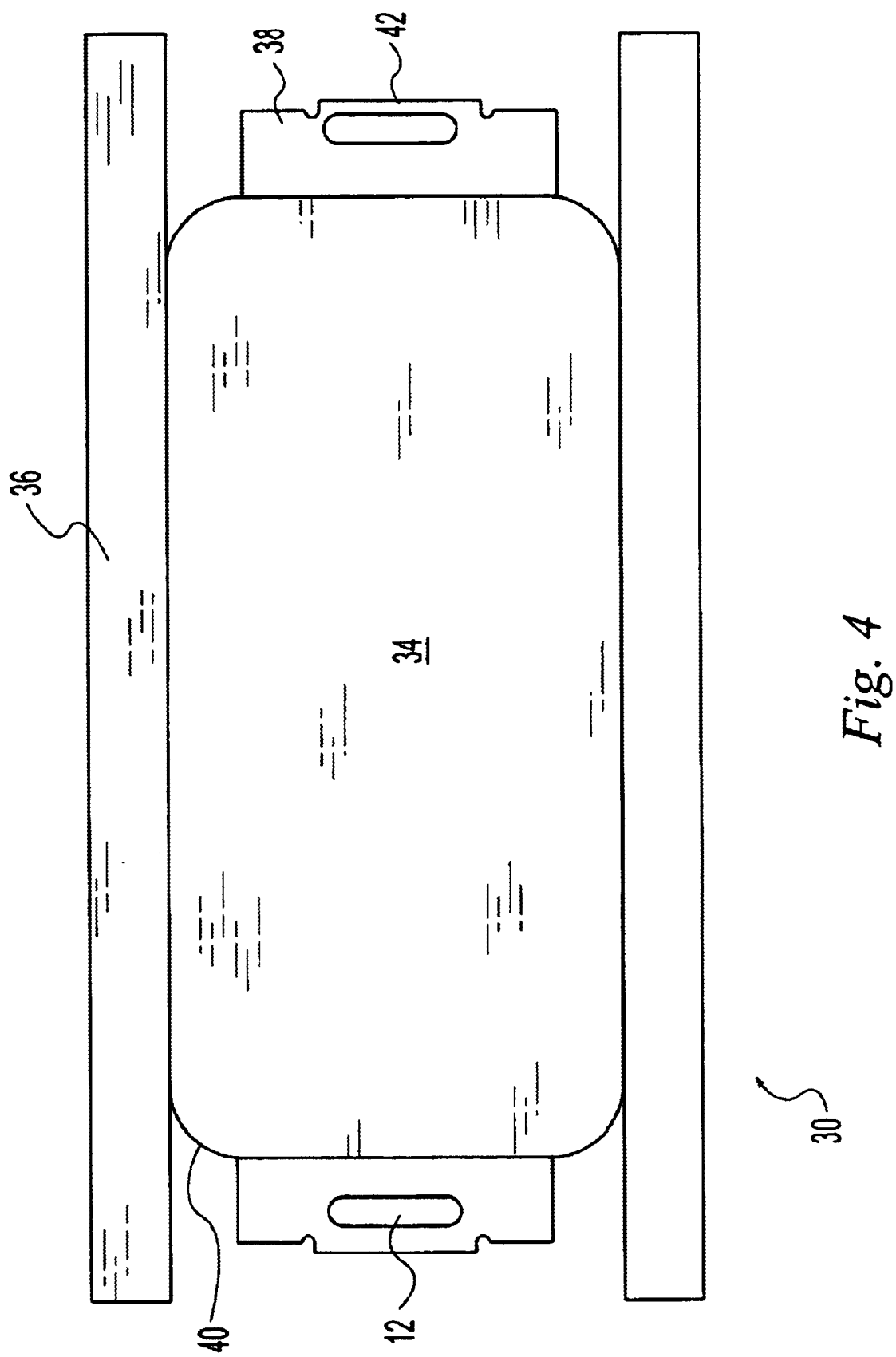
FIG. 4 is a top plan view of a sheet metal stamping prior to folding to form the tray of FIG. 1.

FIGS. 4–7 depict the sheet metal blank 30 and handle insert 14 from which the tray is assembled. As can be seen in FIG. 4, the tray bottom wall 4, side walls 6, and end walls 8 are formed from a single piece of stamped sheet metal. The sheet metal blank 30 includes bottom portion 34, side tabs 36 and end tabs 38. Bottom portion 34 includes rounded corners 40. Side tabs 36 extend beyond the bottom portion 34 at each end. End tabs 38 include elongate handle aperture 12 and upper tab 42.

The tray 2 is formed by first bending a slot 13 in each end of each side tab. The side tabs 36 are then bent upwardly to form a right angle with the bottom portion 34. The side tabs 36 are bent at each end to form the smooth rounded corners 9 and part of the end walls 8. In the exemplary embodiment of FIGS. 2 and 3, the sheet metal blank is shaped to produce a gap 35 separating the side tab 36 and the bottom portion 34. This gap facilitates bending the side tab 36 to match the rounded corners 40 of the bottom portion 34. The upper tabs 42 are each bent to form a right angle with the end tabs 38 thus forming the upper portions 15. The end tabs 38 are bent upwardly to form a right angle with the bottom portion 34 and to overlap the side tabs 36. Preferably the side walls are each bent at each of their ends to form lap joints with the end walls such that the exterior of the side and end walls are flush. Handle insert 14 is placed with attachment ears 11 engaging slots 13 and being trapped within the slots by end tab 38. Aperture 16 is aligned with aperture 12 and upper portion 15 contacts the top of handle insert 14. Preferably a recessed shelf 17 is formed in the top of the handle insert 14 to receive the upper portion 15 so that the top of upper portion 15 is flush with the remaining top of the handle insert. End tab 38 and side tab 36 are riveted 44 together above and below slot 13 to hold the tray in rigid alignment. Alternatives to rivets include screws and weld beads and other attachments known in the art. Preferably no rivets are inserted through the handle insert 14 and the handle insert is allowed some freedom of movement within the slots 13. Thus, when the tray 2 is heated in an autoclave, and the handle inserts 14 and end walls 8 expand different amounts, no breakage occurs.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. A sterilization tray comprising:
   a rectangular bottom wall having rounded corners and having first and second side lengths; first opposing side walls being a continuation of said bottom wall over a portion of said first side length, the first side walls extending up from the bottom wall, the side walls curving inwardly at each end to correspond to the rounded corners of the bottom wall;
   second opposing side walls being a continuation of said bottom wall over a portion of said second side length, the second side walls extending up from the bottom wall, the second opposing side walls being fastened to the first opposing side walls to form a container enclosed on five sides.

2. The sterilization tray of claim 1 wherein said first opposing side walls and second opposing side walls overlap one another and are fastened together where they overlap.

3. The sterilization tray of claim 2 wherein the first opposing side walls are each bent at each of their ends to form lap joints with the second opposing side walls such that the exterior of the first opposing side walls and the exterior of second opposing side walls are flush.

4. The sterilization tray of claim 3 wherein the lap joint is secured by one of the group consisting of rivets, screws and weld beads.

5. The sterilization tray of claim 4 wherein the bottom wall and both pairs of opposing side walls are formed of a single sheet of stamped and bent sheet metal.

6. The sterilization tray of claim 1 wherein each handle insert aperture is bounded at a top by a grip surface having a thickness greater than a thickness of the side wall on which it is attached.

7. The sterilization tray of claim 6 wherein the grip surface is scalloped.

8. The sterilization try of claim 1 wherein each handle insert has a top exterior surface and the end wall on which it is attached includes an upper portion overlying a portion of the top exterior surface such that each handle insert is reinforced on its top exterior surface.

9. The sterilization tray of claim 8 wherein each handle insert further comprises outwardly extending attachment ears and the first opposing side walls include slots such that the attachment ears are trapped within the slots between the first and second opposing side walls, the fit between the attachment ears and slots allowing for differential expansion of the handle insert and the side walls.

10. The sterilization tray of claim 9 wherein each handle insert further comprises upwardly extending stacking lugs and the bottom wall includes corresponding lug receiving holes such that the sterilization tray can be securely stacked atop a like sterilization tray with the lug receiving holes engaging the stacking lugs of the tray below.

11. A sterilization tray comprising:
   a rectangular bottom wall;
   first opposing side walls extending up from the bottom wall;
   second opposing side walls extending up from the bottom wall, the second opposing side walls being fastened to the first opposing side walls to form a container enclosed on five sides, one of the pairs of opposing side walls including in each side wall an elongate handle aperture; and
   a handle insert attached to each end wall, the handle insert having a grip aperture through it, the aperture in the end wall and the aperture in the handle insert communicating with one another.

12. The sterilization tray of claim 11 wherein each handle insert aperture is bounded at a top by a grip surface having a thickness greater than a thickness of the side wall on which it is attached, the grip surface being scalloped.

13. The sterilization tray of claim 12 wherein each handle insert has a top exterior surface and the end wall on which it is attached includes an upper portion overlying a portion of the top exterior surface such that each handle insert is reinforced on its top exterior surface.

14. The sterilization tray of claim 13 wherein each handle insert further comprises outwardly extending attachment ears and the first opposing side walls include slots such that the attachment ears are trapped within the slots between the first and second opposing side walls, the fit between the attachment ears and slots allowing for differential expansion of the handle insert and the side walls.

15. The sterilization tray of claim 11 wherein the bottom and first and second opposing side walls are sheet metal and the handle inserts are a one-piece molded material.

16. The sterilization tray of claim 15 wherein each handle insert further comprises upwardly extending stacking lugs and the bottom wall includes corresponding lug receiving holes such that the sterilization tray can be securely stacked atop a like sterilization tray with the lug receiving holes engaging the stacking lugs of the tray below.

17. The sterilization tray of claim 15 further comprising a molded one-piece foot attached beneath each corner of the bottom wall.

* * * * *